(12) United States Patent
Wen

(10) Patent No.: US 7,448,514 B2
(45) Date of Patent: Nov. 11, 2008

(54) STORAGE SYSTEM FOR DENTAL DEVICES

(75) Inventor: Huafeng Wen, Redwood City, CA (US)

(73) Assignee: Align Technology, Inc., Santa Clara, CA (US)

( * ) Notice: Subject to any disclaimer, the term of this patent is extended or adjusted under 35 U.S.C. 154(b) by 681 days.

(21) Appl. No.: 11/050,051

(22) Filed: Feb. 3, 2005

(65) Prior Publication Data

US 2006/0175272 A1    Aug. 10, 2006

(51) Int. Cl.
    *G07F 11/72*    (2006.01)
(52) U.S. Cl. .......................... 221/30; 221/26; 221/270; 221/274; 221/276; 221/271
(58) Field of Classification Search ............... 221/270, 221/271, 274, 276, 30, 26, 32
    See application file for complete search history.

(56) References Cited

U.S. PATENT DOCUMENTS

| | | | |
|---|---|---|---|
| 1,926,426 A * | 9/1933 | Blake | 221/276 |
| 2,620,250 A * | 12/1952 | Pierson | 221/232 |
| 2,902,187 A * | 9/1959 | Cabanban | 221/240 |
| 4,755,139 A | 7/1988 | Abbatte | |
| 4,781,120 A * | 11/1988 | Farrow et al. | 104/118 |
| 4,798,534 A | 1/1989 | Breads | |
| 4,856,991 A | 8/1989 | Breads | |
| 4,936,862 A | 6/1990 | Walker | |
| 5,011,405 A | 4/1991 | Lemchen | |
| 5,035,613 A | 7/1991 | Breads | |
| 5,055,039 A | 10/1991 | Abbatte | |
| 5,059,118 A | 10/1991 | Breads | |
| 5,186,623 A | 2/1993 | Breads | |
| 5,190,168 A * | 3/1993 | French et al. | 211/59.2 |
| 5,273,429 A | 12/1993 | Rekow | |
| 5,338,198 A | 8/1994 | Wu | |
| 5,340,309 A | 8/1994 | Robertson | |
| 5,342,202 A | 8/1994 | Deshayes | |
| 5,368,478 A | 11/1994 | Andreiko | |
| 5,382,164 A | 1/1995 | Stern | |
| 5,452,219 A | 9/1995 | Dehoff | |
| 5,549,476 A | 8/1996 | Stern | |
| 5,587,912 A | 12/1996 | Andersson | |
| 5,607,305 A | 3/1997 | Andersson | |
| 5,645,421 A | 7/1997 | Slootsky | |
| 5,879,158 A | 3/1999 | Doyle | |
| 5,975,893 A | 11/1999 | Chishti | |
| 6,131,765 A * | 10/2000 | Barry et al. | 221/264 |
| 6,217,325 B1 | 4/2001 | Chishti | |
| 6,227,850 B1 | 5/2001 | Chishti | |
| 6,227,851 B1 | 5/2001 | Chishti | |
| 6,299,440 B1 | 10/2001 | Phan | |
| 6,309,215 B1 | 10/2001 | Phan | |
| 6,497,574 B1 | 12/2002 | Miller | |
| 6,499,997 B2 | 12/2002 | Chishti | |
| 6,514,074 B1 | 2/2003 | Chishti | |
| 6,524,101 B1 | 2/2003 | Phan | |

(Continued)

*Primary Examiner*—Gene O. Crawford
*Assistant Examiner*—Timothy R Waggoner
(74) *Attorney, Agent, or Firm*—Paul, Hastings, Janofsky & Walker LLP

(57) ABSTRACT

A container for storing dental devices includes a container body adapted to hold the dental devices and a dispensing mechanism configured to dispense one of the dental devices when the dispensing mechanism is triggered.

28 Claims, 6 Drawing Sheets

U.S. PATENT DOCUMENTS

| | | |
|---|---|---|
| 6,554,611 B2 | 4/2003 | Chishti |
| 6,572,372 B1 | 6/2003 | Phan |
| 6,582,227 B2 | 6/2003 | Phan |
| 6,582,229 B1 | 6/2003 | Miller |
| 6,602,070 B2 | 8/2003 | Miller |
| 6,607,382 B1 | 8/2003 | Kuo |
| 6,621,491 B1 | 9/2003 | Baumrind |
| 6,626,666 B2 | 9/2003 | Chishti |
| 6,629,840 B2 | 10/2003 | Chishti |
| 6,633,789 B1 | 10/2003 | Nikolskiy |
| 6,665,570 B2 | 12/2003 | Pavloskaia |
| 6,682,346 B2 | 1/2004 | Chishti |
| 6,685,469 B2 | 2/2004 | Chishti |
| 6,685,470 B2 | 2/2004 | Chishti |
| 6,688,886 B2 | 2/2004 | Hughes |
| 6,699,037 B2 | 3/2004 | Chishti |
| 6,705,861 B2 | 3/2004 | Chishti |
| 6,705,863 B2 | 3/2004 | Phan et al. |
| 6,722,880 B2 | 4/2004 | Chishti |
| 6,726,478 B1 | 4/2004 | Isiderio |
| 6,729,876 B2 | 5/2004 | Chishti |

* cited by examiner

STORAGE SYSTEM FOR DENTAL DEVICES

CROSS-REFERENCES TO RELATED INVENTIONS

The present invention is also related to commonly assigned U.S. Patent Application, titled "Methods for producing non-interfering tooth models" by Huafeng Wen and concurrently filed and commonly assigned U.S. Patent Application, titled "Intelligent tracking of dental devices" by Huafeng Wen and concurrently filed.

The present invention is also related to commonly assigned U.S. patent application Ser. No. 11/013,152, titled "A base for physical dental arch model" by Huafeng Wen, filed Dec. 14, 2004, commonly assigned U.S. patent application Ser. No. 11/012,924, titled "Accurately producing a base for physical dental arch model" by Huafeng Wen, filed Dec. 14, 2004, commonly assigned U.S. patent application Ser. No. 11/013, 145, titled "Fabricating a base compatible with physical dental tooth models" by Huafeng Wen, filed Dec. 14, 2004, commonly assigned U.S. patent application Ser. No. 11/013, 156, titled "Producing non-interfering tooth models on a base" by Huafeng Wen, filed Dec. 14, 2004, commonly assigned U.S. patent application Ser. No. 11/11/013,160, titled "System and methods for casting physical tooth model" by Huafeng Wen, filed Dec. 14, 2004, commonly assigned U.S. patent application Ser. No. 11/013,159, titled "Producing a base for accurately receiving dental tooth models" by Huafeng Wen, and filed Dec. 14, 2004, commonly assigned U.S. patent application Ser. No. 11/11/013,157, titled "Producing accurate base for dental arch model" by Huafeng Wen, filed Dec. 14, 2004.

The present invention is also related to commonly assigned U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, filed Nov. 2, 2004. The disclosure of these related applications are incorporated herein by reference.

TECHNICAL FIELD

This application generally relates to the field of dental care, and more particularly to a system and a method for storing dental devices.

BACKGROUND

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

A variety of designs exist in dental brackets and dental aligners. An orthodontic treatment usually include a plurality of treatment step, each of which requires the use of a different aligner or bracket so that the patient's teeth can be moved incrementally to the desired positions. There is a long felt need in the dental care to have a dental storage system that can properly store dental devices such as aligners and brackets for orthodontic treatment of one or more patients.

SUMMARY OF THE INVENTION

The present invention has been devised to provide a practical, effective and efficient methods and apparatus to manufacture and construct the physical dental arch model.

In one aspect, the present invention relates to a container for storing dental devices, comprising:

a container body adapted to hold the dental devices; and a dispensing mechanism configured to dispense one of the dental devices when the dispensing mechanism is triggered.

In another aspect, the present invention relates to a container for storing dental devices, comprising:

a container body adapted to hold the dental devices;

a dispensing mechanism configured to dispense one of the dental devices when the dispensing mechanism is triggered; and a window configured to allow the dispensing of the dental device.

In yet another aspect, the present invention relates to a container for storing dental devices, comprising:

a container body adapted to hold the dental devices;

a window configured to allow the dispensing of the dental device;

a spring enabled dispensing mechanism configured to dispense one of the dental devices stored in the container in a first-in and first-out order when the spring enabled dispensing mechanism is triggered by the pressing of a release button.

Embodiments may include one or more of the following advantages. A dispensing system is provided for storing dental devices such a dental aligners. The dental devices are securely stored in a container body to protect them from damage. The dispensing system is convenient, compact and portable. The dispensing system can maintain a fixed FIFO order of the stored dental devices. The dispensing system can automatically release the dental devices by simply pushing a release button. The dispensing system can serve as a useful tool in orthodontic treatment.

The details of one or more embodiments are set forth in the accompanying drawing and in the description below. Other features, objects, and advantages of the invention will become apparent from the description and drawings, and from the claims.

BRIEF DESCRIPTION OF THE DRAWINGS

The accompanying drawing, which are incorporated in and form a part of this specification, illustrate embodiments of the invention and, together with the description, serve to explain the principles of the invention.

DESCRIPTION OF INVENTION

Figure 1:
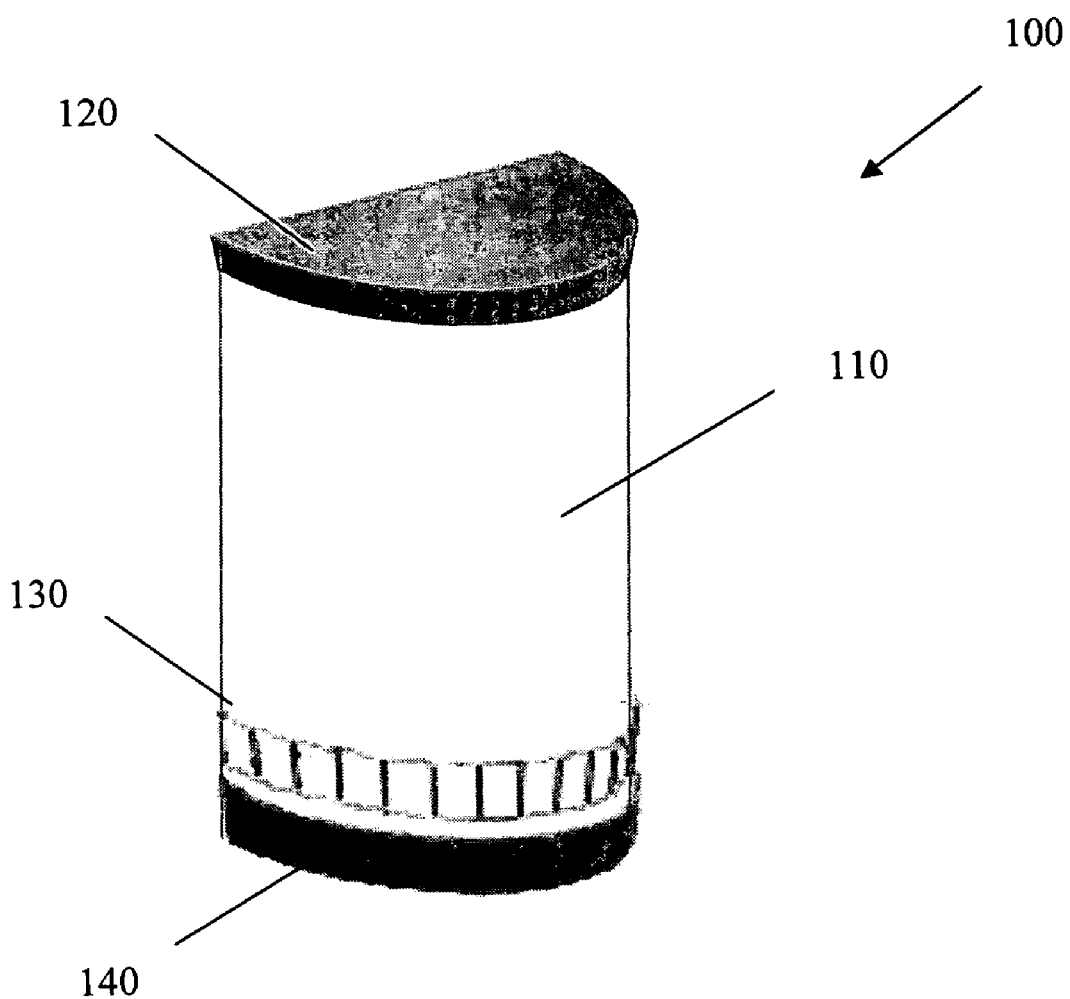
FIG. 1 is a dispensing container for dental devices in accordance with the present invention.

As shown in FIG. 1, a dispensing container 100 for dental devices includes a container body 110, a container cap 120 that can seal the upper end of the container body 110, a dispensing window 130 in the lower front side, and a release button 140. The dispensing container 100 can store dental devices such as dental aligners, dental brackets, dental arch models, tooth models, and bases or base components for tooth models. The dental devices can stack up on each other inside the container body 110. The dental devices can pop out of the dispensing window 130 by pushing the release button 140. The dental devices are stored in the order they were stored, that is, "First In, First Out" (FIFO). The container body 110 can be cylindrically shaped and made of a waterproof material that can withstand rough handling such that the dental devices stored in the container will not be damaged if the container is accidentally dropped on to the floor.

Details of the fabrication of the dental aligners, dental arch models, dental tooth models, and bases for tooth models are disclosed in commonly assigned and above referenced commonly assigned U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, filed Nov. 2, 2004, the content of which is incorporated herein by reference.

Figure 2:
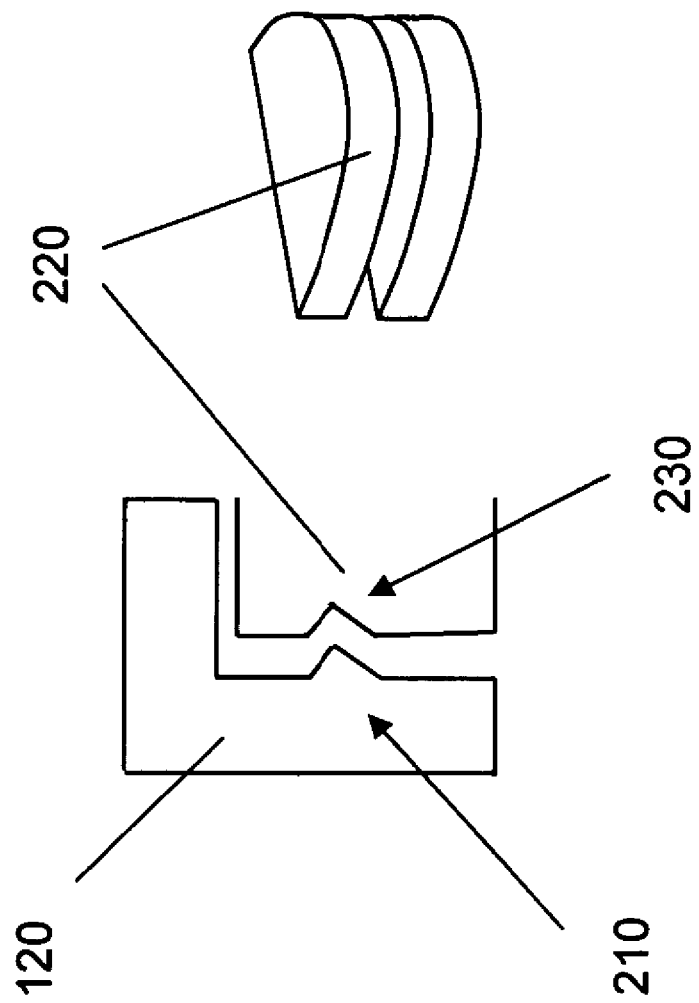
FIG. 2 illustrates the locking mechanism of the container cap at the upper end of the container body.
Figure 3:
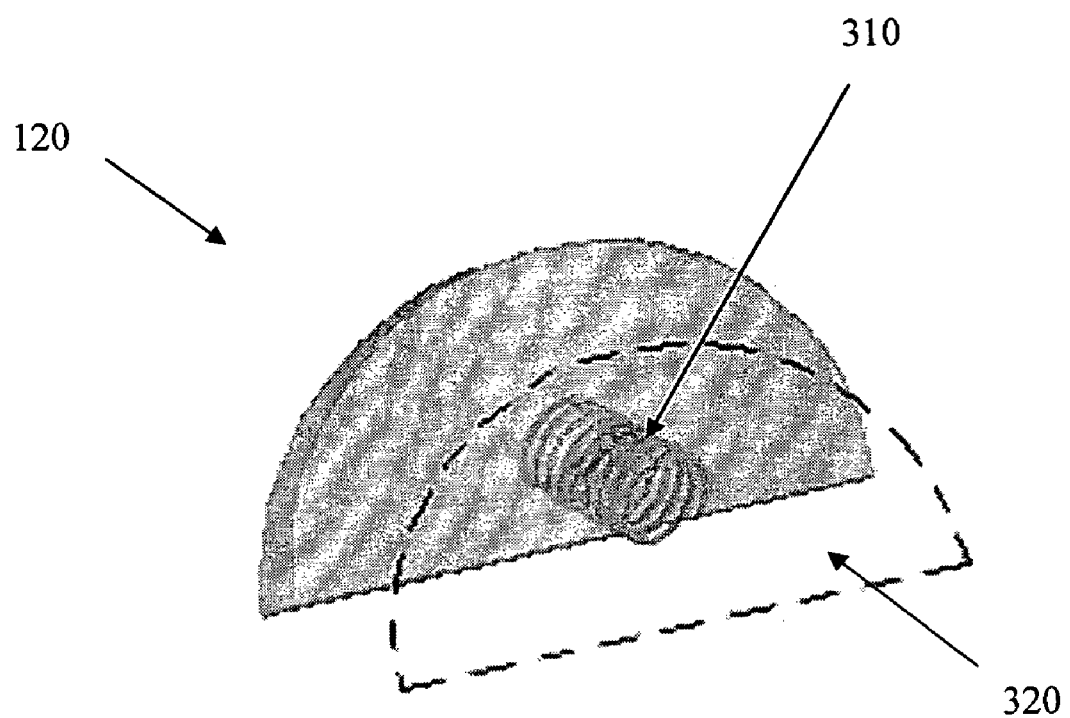
FIG. 3 illustrates a spring load mechanism on the underside of the container cap.

The container cap 120, as shown in FIG. 2, is constructed so that it can snap to be closed. The upper end 220 of the dispensing container 100 includes a groove 230 around its rim. The inner face of the container cap 120 includes a protrusion 210 that fits the groove 230. When the container cap 120 is pressed down in the upper end 220 of the dispensing body 110, the protrusion 210 snaps into the groove 230 to lock the container cap 120 to the container body 110.

The container cap 120 includes a tensile spring 310 fixed to its underside. A pressure plate 320 is connected to the end of the spring 310. The spring loaded pressure plate 320 pushes the dental devices stored in the container body 110 downward to ensure the dental devices to be tightly packed inside the container body 110. The spring load also enables the dental device at the bottom to be always registered to the dispensing window 130. When uncompressed, the spring 310 can reach the bottom of the container body 110 such that the last dental device in the container body 110 can be dispensed through the dispensing window 130.

Figure 4:
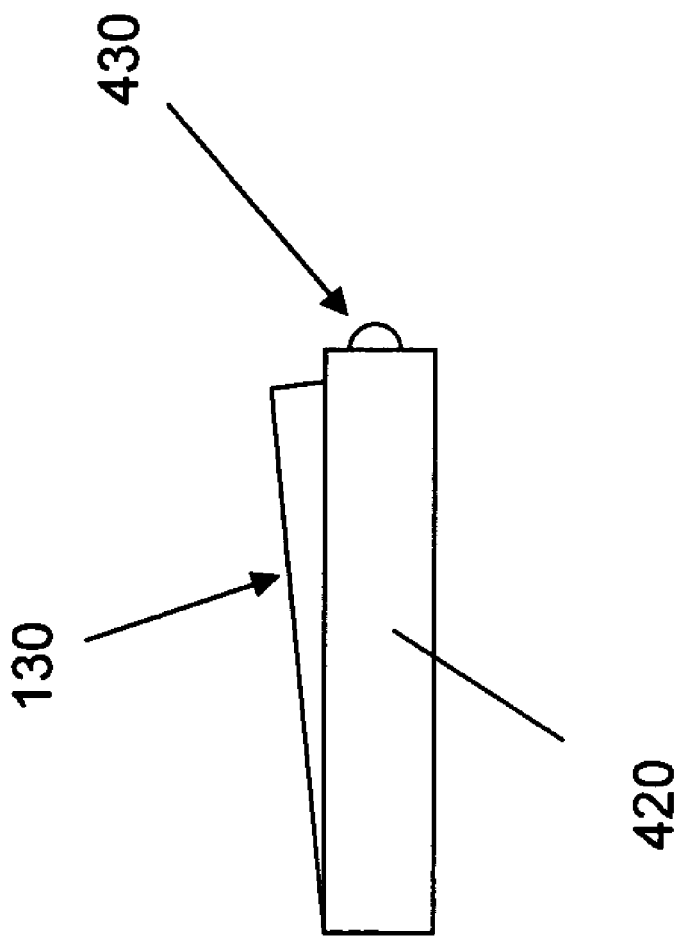
FIG. 4 shows a door for the dispensing window in the front near the lower end of the dispensing container.

The dispensing window 130 can be closed by a door 420 as shown in FIG. 4. The door 420 can be locked by a latch 430 fixed on the door 420 to prevent dental devices from falling out of the container body 110. Alternatively, the door 420 can also be kept closed by a spring mechanism that automatically closes the dispensing window 130 after each extraction of a dental device.

Figure 5:
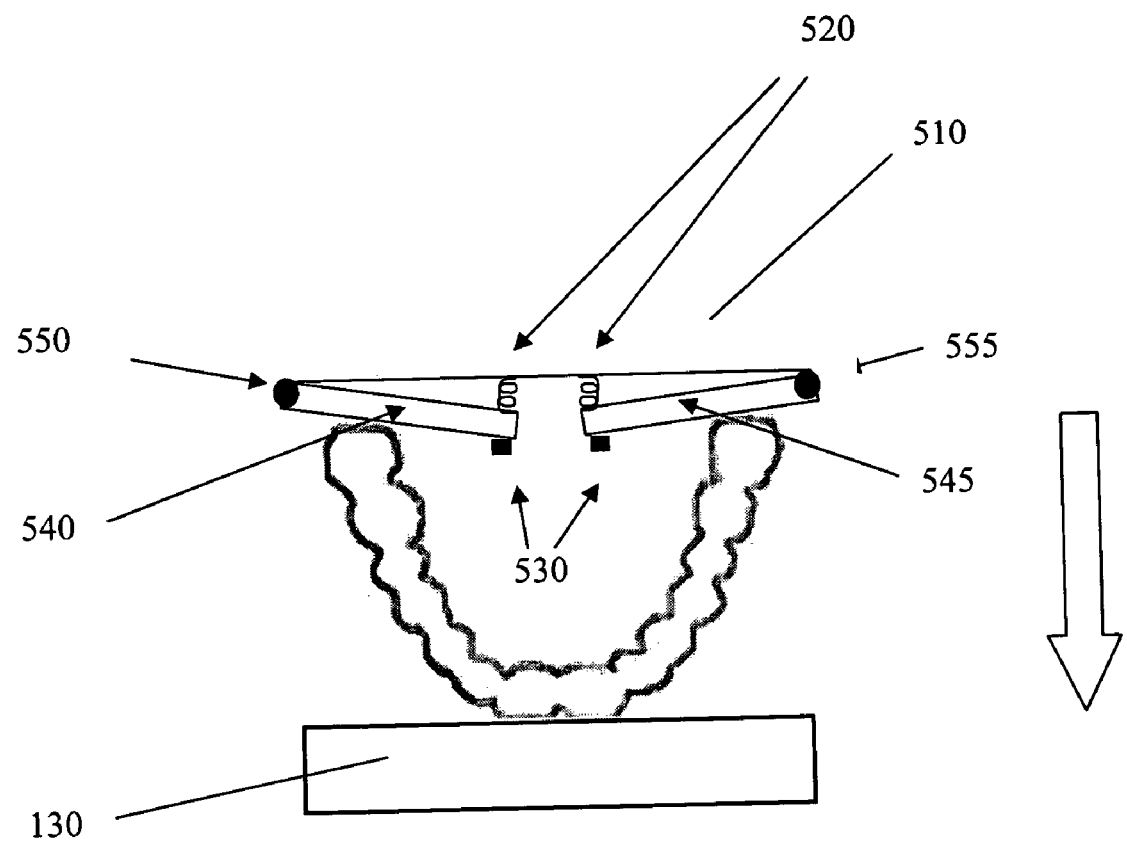
FIG. 5 illustrate an dispensing mechanism for dispensing dental devices from the dispensing container.

The dispensing container 100 includes a dispensing mechanism. As shown in FIG. 1 and FIG. 5, the automatic dispensing mechanism includes a release button 140 located right below the dispensing window 130. The release button 140 is attached to a spring. Two more springs 520 are attached to the back wall 510 of the container body 110. The ends of the springs 520 are attached to stoppers 530 and pushing sticks 540, 545 that are hinged at hinges 550, 555.

When the release button 140 is pressed, the spring attached to it is compressed, the stoppers 530 move forwards causing the pushing sticks 540, 545 to move forward. This forward motion moves the bottom most dental device in the container body 100 to partially move out of the dispensing window 130. As soon as the partially popped out dental device is removed, the springs 520 retract, moving the push sticks 540, 545 to the initial positions. The dental devices above are pushed downwards by the spring 310 on the container cap 120. The spring attached to the release button 140 returns to its normal position, pushing the release button 140 outwards. This motion causes the stoppers to return to their respective positions as well. The dispensing container 100 is now ready to dispense another dental device. The described arrangement allows only one dental device such as an aligner to be dispensed at a time.

In one embodiment, a packaging station is included at the bottom of the dispensing container 100. The dispensed dental device is packaged in a packaging material before it is removed from the container 100.

Figure 6:
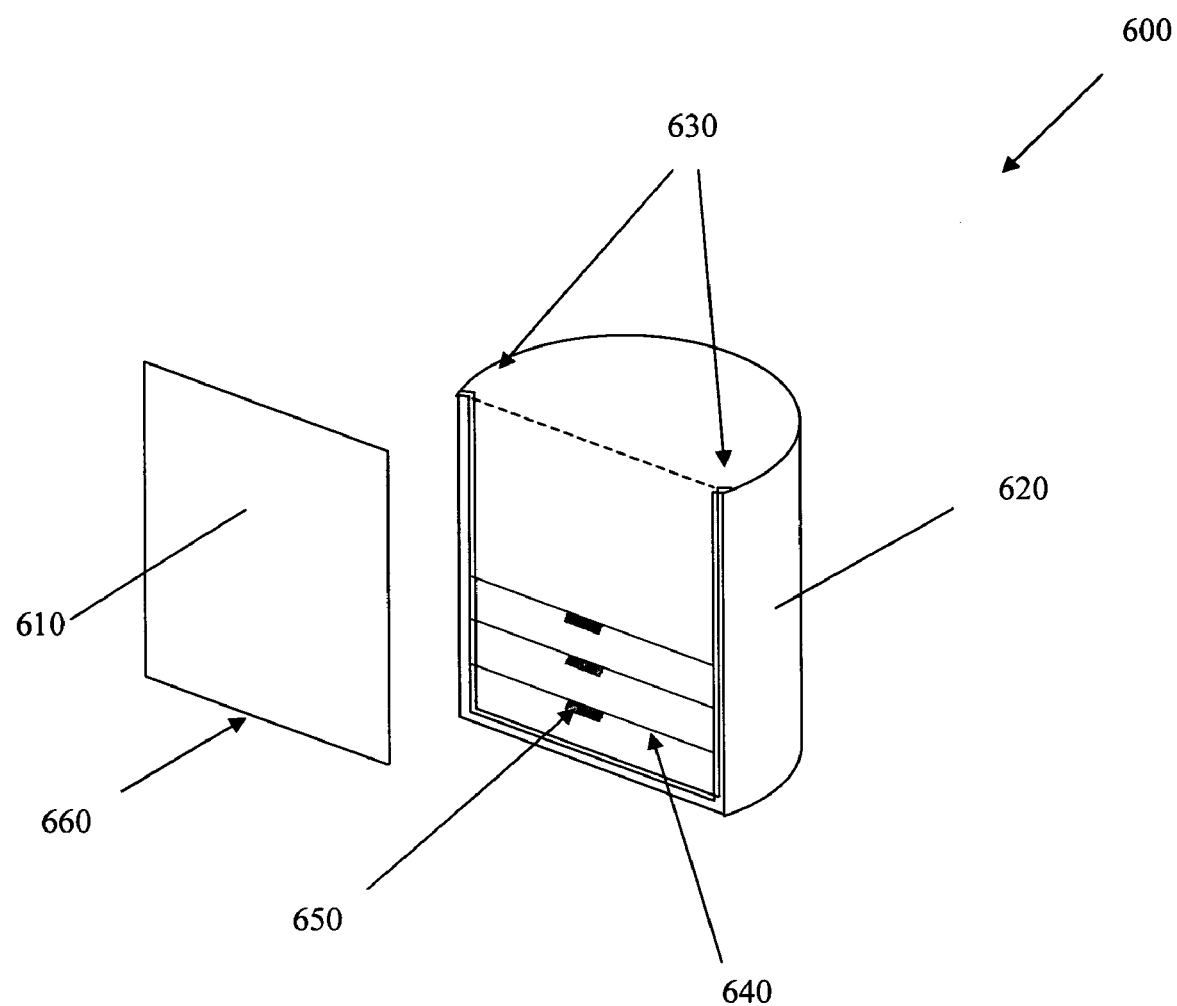
FIG. 6 illustrates a slide-able back for the dispensing container.

In another embodiment, the dispensing container 600 includes a slide-able door 610 on the back of the container 620, as shown in FIG. 6. The slide-able door 610 can slide into slots 630 on the container body 620. The dental devices 640 are packed in a stack in FIFO order. The dental devices 640 can be tagged by tags 650 that can be barcodes or RFID devices. The tags 650 are facing backward such that they can be read or scanned once the slide-able door 610 slides open. The tags can also be replaced or changed if the plans for the dental devices are changed.

In another embodiment, the lower edge 660 of the slide-able door 610 has a sharp edge that can be is used to cut off packaging material of the dental devices. The cut-open packages containing the dental devices can be dispensed and conveniently taken out of the package by a user.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A container for storing dental devices, comprising:
   a container body adapted to hold the dental devices;
   a dispensing mechanism configured to dispense one of the dental devices when the dispensing mechanism is triggered; and
   a slide-able door capable of cutting packaging material.

2. The container of claim 1, wherein the dispensing mechanism comprises a spring mechanism that is configured to dispense one of the dental devices stored in the container.

3. The container of claim 1, wherein the dispensing mechanism is triggered by the pressing of a release button.

4. The container of claim 1, wherein the dispensing mechanism includes a window configured to allow the dispensing of the dental device.

5. The container of claim 1, wherein the dental devices are stored in a fixed order in the container.

6. The container of claim 1, wherein the dental devices stored in the container are dispensed by the dispensing mechanism in a first-in and first-out order.

7. The container of claim 1, wherein the container body can hold three or more dental devices.

8. The container of claim 1, further comprising a container cap that can be locked to the container body and seal the dental devices inside the container body.

9. The container of claim 1, wherein the dental devices stored in the container body include one or more of dental aligners, dental brackets, dental arch models, tooth models, and bases or base components for tooth models.

10. The container of claim 1, wherein the dental devices stored in the container each comprise a barcode or radio-frequency identification device tag.

11. The container of claim 1, further comprising a packaging station for packaging one or more of the dental devices in a packaging material before removal from the container body.

12. The container of claim 1, wherein at least one of the dental devices is packaged in a packaging material within the container body.

13. The container of claim 1, wherein at least one of the dental devices is packaged in a packaging material upon removal from the container body.

14. A container for storing dental devices, comprising:
    a container body adapted to hold the dental devices;
    a dispensing mechanism configured to dispense one of the dental devices when the dispensing mechanism is triggered; and
    a window configured to allow the dispensing of the dental device; and
    a slide-able door capable of cutting packaging material.

15. The container of claim 14, wherein the dispensing mechanism comprises a spring mechanism that is configured to dispense one of the dental devices stored in the container when the dispensing mechanism is triggered by the pressing of a release button.

16. The container of claim 14, wherein the dental devices stored in the container are dispensed by the dispensing mechanism in a first-in and first-out order.

17. The container of claim 14, further comprising a container cap that can be locked to the container body and seal the dental devices inside the container body.

18. The container of claim 14, wherein the dental devices stored in the container body include one or more dental aligners, dental brackets, dental arch models, tooth models, and bases or base components for tooth models.

19. The container of claim 14, wherein the dental devices stored in the container each comprise a barcode or radio-frequency identification device tag.

20. The container of claim 14, further comprising a packaging station for packaging one or more of the dental devices in a packaging material before removal from the container body.

21. The container of claim 14, wherein at least one of the dental devices is packaged in a packaging material within the container body.

22. The container of claim 14, wherein at least one of the dental devices is packaged in a packaging material upon removal from the container body.

23. A container for storing dental devices, comprising:
    a container body adapted to hold the dental devices;
    a window configured to allow the dispensing of the dental device;
    a spring enabled dispensing mechanism configured to dispense one of the dental devices stored in the container in a first-in and first-out order when the spring enabled dispensing mechanism is triggered by the pressing of a release button; and
    a slide-able door capable of cutting packaging material.

24. The container of claim 23, wherein the dental devices stored in the container body include one or more of dental aligners, dental brackets, dental arch models, tooth models, and bases or base components for tooth models.

25. The container of claim 23, wherein the dental devices stored in the container each comprise a barcode or radio-frequency identification device tag.

26. The container of claim 23, further comprising a packaging station for packaging one or more of the dental devices in a packaging material before removal from the container body.

27. The container of claim 23, wherein at least one of the dental devices is packaged in a packaging material within the container body.

28. The container of claim 23, wherein at least one of the dental devices is packaged in a packaging material upon removal from the container body.

* * * * *

UNITED STATES PATENT AND TRADEMARK OFFICE
CERTIFICATE OF CORRECTION

PATENT NO. : 7,448,514 B2  
APPLICATION NO. : 11/050051  
DATED : November 11, 2008  
INVENTOR(S) : Huafeng Wen Page 1 of 1

It is certified that error appears in the above-identified patent and that said Letters Patent is hereby corrected as shown below:

Column 5, line 42-49 (claim 14),

Claim 14 should read:

A container for storing dental devices, comprising:
    a container body adapted to hold the dental devices;
    a dispensing mechanism configured to dispense one of the dental devices when the dispensing mechanism is triggered;
    a window configured to allow the dispensing of the dental device; and
    a slide-able door capable of cutting packaging material.

Signed and Sealed this

Twenty-seventh Day of January, 2009

JOHN DOLL  
*Acting Director of the United States Patent and Trademark Office*